United States Patent
Tung

(10) Patent No.: US 9,840,463 B2
(45) Date of Patent: *Dec. 12, 2017

(54) DEUTERATED RIGOSERTIB

(71) Applicant: Concert Pharmaceuticals, Inc., Lexington, MA (US)

(72) Inventor: Roger D. Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/010,961

(22) Filed: Jan. 29, 2016

(65) Prior Publication Data

US 2016/0159736 A1 Jun. 9, 2016

Related U.S. Application Data

(63) Continuation of application No. 14/395,795, filed as application No. PCT/US2013/037426 on Apr. 19, 2013, now Pat. No. 9,249,093.

(60) Provisional application No. 61/636,462, filed on Apr. 20, 2012, provisional application No. 61/782,367, filed on Mar. 14, 2013.

(51) Int. Cl.
| | | |
|---|---|---|
| *A01N 41/10* | (2006.01) | |
| *A61K 31/10* | (2006.01) | |
| *C07C 317/10* | (2006.01) | |
| *A61K 31/519* | (2006.01) | |
| *A61K 31/444* | (2006.01) | |
| *A61K 31/4439* | (2006.01) | |
| *C07C 317/28* | (2006.01) | |
| *A61K 31/136* | (2006.01) | |
| *A61K 31/18* | (2006.01) | |
| *A61K 31/197* | (2006.01) | |
| *A61K 31/255* | (2006.01) | |
| *A61K 45/06* | (2006.01) | |
| *A61K 31/165* | (2006.01) | |
| *C07B 59/00* | (2006.01) | |

(52) U.S. Cl.
CPC .......... *C07C 317/10* (2013.01); *A61K 31/136* (2013.01); *A61K 31/165* (2013.01); *A61K 31/18* (2013.01); *A61K 31/197* (2013.01); *A61K 31/255* (2013.01); *A61K 31/444* (2013.01); *A61K 31/4439* (2013.01); *A61K 31/519* (2013.01); *A61K 45/06* (2013.01); *C07B 59/001* (2013.01); *C07C 317/28* (2013.01); *C07B 2200/05* (2013.01)

(58) Field of Classification Search
None
See application file for complete search history.

(56) References Cited

U.S. PATENT DOCUMENTS

| | | |
|---|---|---|
| 6,221,335 B1 | 4/2001 | Foster |
| 6,440,710 B1 | 8/2002 | Keinan et al. |
| 6,603,008 B1 | 8/2003 | Ando et al. |
| 7,517,990 B2 | 4/2009 | Ito et al. |
| 7,598,232 B2 | 10/2009 | Reddy et al. |
| 9,249,093 B2 | 2/2016 | Tung |
| 2007/0082929 A1 | 4/2007 | Gant et al. |
| 2007/0197695 A1 | 8/2007 | Potyen et al. |
| 2008/0103122 A1 | 5/2008 | Veltri |

FOREIGN PATENT DOCUMENTS

| | | |
|---|---|---|
| WO | WO 95/26325 A2 | 10/1995 |
| WO | WO 2007/118651 A1 | 10/2007 |
| WO | WO 2012/009446 A1 | 1/2012 |
| WO | WO 2013/159026 A1 | 4/2013 |

OTHER PUBLICATIONS

Weissleder et al. Nature (2008), vol. 452, pp. 580-589.*
Baille, T. A., "The Use of Stable Isotopes in Pharmacological Research," *Pharmacological Reviews*, 33(2): 81-132 (1981).
Browne, T. R., "Stable Isotope Techniques in Early Drug Development: An Economic Evaluation," *J. Clin. Pharmacol.*, 38: 213-220 (1998).
Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).
Dyck, L. E., et al., "Effects of Deuterium Substitution on the Catabolism of β-Phenylethylamine: An In Vivo Study," *Journal of Neurochemistry*, 46(2): 399-404 (1986).
Fisher, M.B. et al., "The Complexities Inherent in Attempts to Decrease Drug Clearance by Blocking Sites of CYP-Mediated Metabolism," *Curr. Opin. Drug Discov. Devel.*, 9(1):101-109 (2006).
Foster, A. B., "Deuterium Isotope Effects in Studies of Drug Metabolism," *Trends in Pharmacological Sciences*, 5: 524-527 (1984).
Foster, A. B., "Deuterium Isotope Effects in the Metabolism of Drugs and Xenobiotics: Implications for Drug Design," *Advances in Drug Research*, 14: 1-40 (1985).
Gouyette, A., "Synthesis of Deuterium-labelled Elliptinium and its Use in Metabolic Studies," *Biomedical and Environmental Mass Spectrometry*, 15: 243-247 (1988).
Haskins, N. J., "The Application of Stable Isotopes in Biomedical Research," *Biomedical Mass Spectrometry*, 9(7): 269-277 (1982).
Honma S., et al., "The Metabolism of Roxatidine Acetate Hydrochloride," *Drug Metabolism and Disposition*, 15(4): 551-559 (1987).

(Continued)

*Primary Examiner* — Patrick T Lewis
(74) *Attorney, Agent, or Firm* — Hamilton, Brook, Smith & Reynolds, P.C.

(57) ABSTRACT

This invention relates to novel substituted styryl benzylsulfones that are multikinase inhibitors and pharmaceutically acceptable acid addition salts thereof. The invention also provides compositions comprising a compound of this invention and the use of such compositions in methods of treating diseases and conditions beneficially treated by an agent that inhibits kinases, such as phosphatidylinositol 3-kinase (PI3-K) and polo-like kinase (PLK-1).

23 Claims, No Drawings

(56) References Cited

OTHER PUBLICATIONS

Kushner, D.J. et al., "Pharmacological Uses and Perspectives of Heavy Water and Deuterated Compounds," *Can. J. Physiol. Pharmacol.*, 77:79-88 (1999).

Pieniaszek, H. J., et al., "Moricizine Bioavailability via Simultaneous, Dual, Stable Isotope Administration: Bioequivalence Implications," *J. Clin. Pharmacol*, 39: 817-825 (1999).

Tonn G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).

Wolen, R. L., "The Application of Stable Isotopes to Studies of Drug Bioavailability and Bioequivalence," *J. Clin. Pharmacol.*, 26: 419-424 (1986).

International Preliminary Report on Patentability for PCT/US2013/037426, entitled "Deuterated Rigosertib", dated Oct. 21, 2014.

International Search Report and Written Opinion for PCT/US2013/037426, entitled "Deuterated Rigosertib", dated Jul. 16, 2013.

\* cited by examiner

DEUTERATED RIGOSERTIB

RELATED APPLICATIONS

This application is a continuation of U.S. application Ser. No. 14/395,795, which is the U.S. National Stage of International Application No. PCT/US2013/037426, filed on Apr. 19, 2013, published in English, which claims the benefit of U.S. Provisional Application No. 61/636,462, filed on Apr. 20, 2012 and U.S. Provisional Application No. 61/782,367, filed on Mar. 14, 2013. The entire teachings of the above applications are incorporated herein by reference.

BACKGROUND OF THE INVENTION

Many current medicines suffer from poor absorption, distribution, metabolism and/or excretion (ADME) properties that prevent their wider use. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated decreased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

SUMMARY OF THE INVENTION

This invention relates to novel substituted styryl benzylsulfones that are multikinase inhibitors and pharmaceutically acceptable acid addition salts thereof. The invention also provides compositions comprising a compound of this invention and the use of such compositions in methods of treating diseases and conditions beneficially treated by an agent that inhibits kinases, such as phosphatidylinositol 3-kinase (PI3-K) and polo-like kinase (PLK-1).

Rigosertib is a substituted styryl benzylsulfone that inhibits multiple kinases including phosphatidylinositol 3-kinase (PI3-K) and polo-like kinase 1 (PLK-1). Phase 1 and 2 studies have demonstrated its ability to delay transition of myelodysplastic syndrome (MDS) to acute myelogenous leukemia (AML), which is a serious disease associated with high mortality. As a result, it is being studied in a Phase 3 trial in MDS patients who have failed previous chemotherapy with accepted agents (ClinicalTrials.gov study NCT01241500).

Rigosertib has also demonstrated activity against solid tumors in combination with gemcitabine in patients whose disease has previously progressed on gemcitabine therapy (Ma W W et al., Clin. Cancer Res. Published online 14 Feb. 2012). It is currently being studied in a Phase 2/3 clinical trial in pancreatic cancer (ClinicalTrials.gov study NCT01360853).

Despite the activity of rigosertib in treating these serious diseases, there remains need for improvement in their therapy.

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" is meant any condition or disorder that damage or interferes with the normal function of a cell, tissue, or organ.

It will be recognized that some variation of natural isotopic abundance occurs in a synthesized compound depending upon the origin of chemical materials used in the synthesis. Thus, a preparation of rigosertib will inherently contain small amounts of deuterated isotopologues. The concentration of naturally abundant stable hydrogen isotopes, notwithstanding this variation, is small and immaterial with respect to the degree of stable isotopic substitution of compounds of this invention. See for instance Wada, E and Hanba, Y, Seikagaku, 1994, 66: 15; Gannes, L Z et al, Comp Biochem Physiol A Mol Integr Physiol, 1998, 119: 725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

"Halogen" means a chloro, bromo, fluoro, or iodo group.

"Alkyl" means a saturated aliphatic hydrocarbon group which may be straight or branched having 1 to 15 carbon atoms in the chain. Exemplary alkyl groups have 1 to 12 carbon atoms in the chain, such as 1 to 6 carbon atoms. Exemplary alkyl groups include methyl, ethyl, n-propyl, i-propyl, n-butyl, t-butyl, n-pentyl, 3-pentyl, heptyl, octyl, nonyl, decyl and dodecyl.

"Alkenyl" means an unsaturated aliphatic hydrocarbon group which may be straight or branched having 2 to 15 carbon atoms in the chain. Exemplary alkenyl groups have 2 to 12 carbon atoms in the chain, such as 2 to 6 carbon atoms. Exemplary alkenyl groups include vinyl, 1-propenyl, 2-propenyl, 1-butenyl, 2-butenyl, and isobutenyl.

"Alkadienyl" means a di-unsaturated aliphatic hydrocarbon group which may be straight or branched having 4 to 15 carbon atoms in the chain. Exemplary alkadienyl groups have 4 to 12 carbon atoms in the chain, such as 4 to 8 carbon atoms. Exemplary alkadienyl groups include 1,3-butadienyl and 1,3-pentatrienyl.

"Aryl" means an aromatic carbocyclic group, which may be monocyclic or bicyclic, preferably containing 6 to 10 carbon atoms. Exemplary aryl groups include phenyl or naphthyl.

"Heteroaryl" means an aromatic group, preferably a 5- to 10-membered aromatic group, which may be monocyclic or bicyclic, in which at least one ring atom is a heteroatom which is nitrogen, oxygen or sulfur. Exemplary heteroaryl groups include pyrazinyl, furanyl, thienyl, pyridyl, pyrimidinyl, isoxazolyl, isothiazolyl, pyridazinyl, 1,2,4-triazinyl, quinolinyl, and isoquinolinyl.

"Heterocycloalkyl" means a non-aromatic group, which may be monocyclic or bicyclic, in which at least one ring atom is a heteroatom which is nitrogen, oxygen or sulfur. Exemplary monocyclic groups are 3- to 6-membered. Exemplary bicyclic groups have at least one 3- to 6-membered ring. Exemplary heterocycloalkyl groups include pyrrolidinyl, piperidinyl, tetrahydropyranyl, tetrahydrofuranyl, tetrahydrothiopyranyl, and tetrahydrothiofuranyl.

The invention also provides salts of the compounds of the invention.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

The compounds of the present invention may contain one or more asymmetric carbon atoms. As such, a compound of this invention can exist as the individual enantiomers as well a mixture of enantiomers. Accordingly, a compound of the present invention will include not only a racemic mixture, but also individual respective enantiomers substantially free of other enantiomers. The term "substantially free of other enantiomers" as used herein means less than 25% of other enantiomers, preferably less than 10% of other enantiomers, more preferably less than 5% of other enantiomers and most preferably less than 2% of other enantiomers are present. Methods of obtaining or synthesizing enantiomers are well known in the art and may be applied as practicable to final compounds or to starting material or intermediates.

Unless otherwise indicated when a disclosed compound is named or depicted by a structure without specifying the stereochemistry and has one or more chiral centers, it is understood to represent all possible stereoisomers of the compound.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert and "t-" each refer to tertiary. "US" refers to the United States of America.

A group is "substituted with" a substituent when one or more hydrogen atoms of the group are replaced with a corresponding number of substituent atoms (if the substituent is an atom) or groups (if the substituent is a group). For example, "substituted with deuterium" refers to the replacement of one or more hydrogen atoms with a corresponding number of deuterium atoms.

Throughout this specification, a variable may be referred to generally (e.g., "each Y") or may be referred to specifically (e.g., $Y^1$, $Y^2$, $Y^3$, etc.). Unless otherwise indicated, when a variable is referred to generally, it is meant to include all specific embodiments of that particular variable.

Therapeutic Compounds

According to one embodiment, the present invention provides a compound of Formula II:

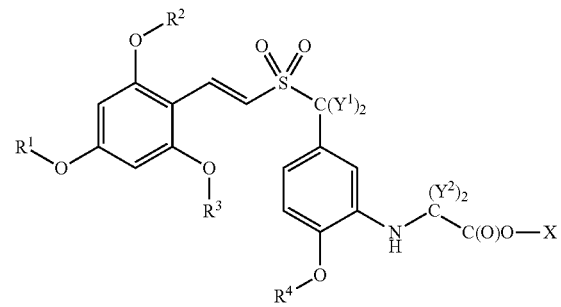

II or a pharmaceutically acceptable salt thereof wherein $R^1$ is $CD_3$ or $CH_3$;

$R^2$ is $CD_3$ or $CH_3$;

$R^3$ is $CD_3$, $CH_3$ or $R^2$;

$R^4$ is $CD_3$ or $CH_3$;

each $Y^1$ is independently hydrogen or deuterium;

each $Y^2$ is independently hydrogen or deuterium;

X is hydrogen, $C_1$-$C_7$ alkyl, $C_2$-$C_7$ alkenyl, $C_2$-$C_7$ alkadienyl, $C_6$-$C_{10}$ aryl or 5- to 10-membered heteroaryl, wherein X is optionally substituted with one or more substituents independently selected from halogen, a —O$C_1$-$C_6$ alkyl group, a 5- to 10-membered heteroaryl group and a 3- to 10-membered heterocycloalkyl wherein the heterocycloalkyl group is optionally substituted with one or more $C_1$-$C_2$ alkyl groups, and wherein if X is $C_1$-$C_7$ alkyl, one or two carbons of the $C_1$-$C_7$ alkyl are optionally replaced with —$NR^5$, and one carbon of the $C_1$-$C_7$ alkyl other than the carbon bonded to the —C(O)O— group of formula II is optionally replaced with oxygen;

each $R^5$ is hydrogen or $C_1$-$C_4$ alkyl optionally substituted with $R^6$; and each $R^6$ is ($C_1$-$C_4$ alkyl)NH; ($C_1$-$C_4$ alkyl)$_2$N, wherein the ($C_1$-$C_4$) alkyl groups in the ($C_1$-$C_4$ alkyl)$_2$N are the same or different; 3- to 10-membered heterocycloalkyl optionally substituted with $C_1$-$C_2$ alkyl; or O$C_1$-$C_4$ alkyl;

provided that if each R1, R2, R3, and R4 are each $CH_3$ and each $Y^1$ is hydrogen, then at least one $Y^2$ is deuterium.

In one embodiment of the compound of formula II, $R^3$ has the value $R^2$ (i.e., $R^2$ and $R^3$ are the same) and the compound of Formula II is a compound of Formula IIa:

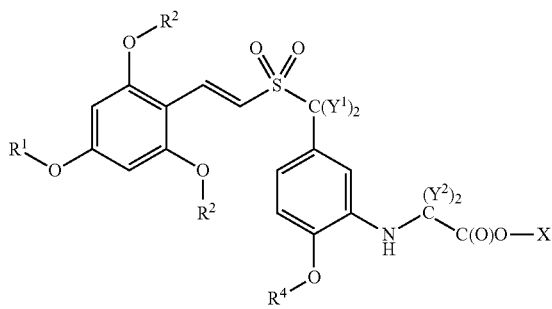

or a pharmaceutically acceptable salt thereof.

In one embodiment of the compound of formula IIa, $R^2$ is $CD_3$. In one aspect of this embodiment, $R^1$ is $CD_3$. In another aspect of this embodiment, $R^1$ is $CH_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of formula IIa is a carboxylic acid. In another aspect, the compound of formula IIa is a pharmaceutically acceptable salt of the carboxylic acid, such as the sodium salt.

In another embodiment of the compound of formula IIa, $R^2$ is $CH_3$. In one aspect of this embodiment, $R^1$ is $CD_3$. In another aspect of this embodiment, $R^1$ is $CH_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of formula IIa is a carboxylic acid. In another aspect, the compound of formula IIa is a pharmaceutically acceptable salt of the carboxylic acid, such as the sodium salt.

In one embodiment of the compound of formula IIa, $R^1$ is $CD_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of formula IIa is a carboxylic acid. In another aspect, the compound of formula IIa is a pharmaceutically acceptable salt of the carboxylic acid, such as the sodium salt.

In one embodiment of the compound of formula IIa, $R^1$ is $CH_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of formula IIa is a carboxylic acid. In another aspect, the compound of formula IIa is a pharmaceutically acceptable salt of the carboxylic acid, such as the sodium salt.

In another embodiment of the compound of formula IIa, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of formula IIa is a carboxylic acid. In another aspect, the compound of formula IIa is a pharmaceutically acceptable salt of the carboxylic acid, such as the sodium salt.

In one embodiment of the compound of formula IIa, $R^4$ is $CD_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of formula IIa is a carboxylic acid. In another aspect, the compound of formula IIa is a pharmaceutically acceptable salt of the carboxylic acid, such as the sodium salt.

In another embodiment of the compound of formula IIa, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of formula IIa is a carboxylic acid. In another aspect, the compound of formula IIa is a pharmaceutically acceptable salt of the carboxylic acid, such as the sodium salt.

In one embodiment of the compound of formula IIa, $R^2$ and $R^1$ are the same. In one aspect of this embodiment, $R^2$ and $R^1$ are $CD_3$. In another aspect of this embodiment, $R^2$ and $R^1$ are $CH_3$.

In one embodiment, X is $C_1$-$C_7$ alkyl optionally substituted with one or more substituents independently selected from halogen, an —$OC_1$-$C_6$ alkyl group, a 5- to 10-membered heteroaryl group and a 3- to 10-membered heterocycloalkyl wherein the heterocycloalkyl group is optionally substituted with one or more $C_1$-$C_2$ alkyl groups. In one aspect of this embodiment, X is methyl, ethyl, N-morpholinoethyl, $N^1$—($N^4$-methylpiperidinyl)ethyl, pyridylmethyl,

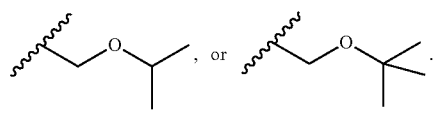

In another set of embodiments, any atom not designated as deuterium in any of the embodiments or aspects set forth above is present at its natural isotopic abundance.

According to one embodiment, the present invention provides a compound of Formula I:

(I)

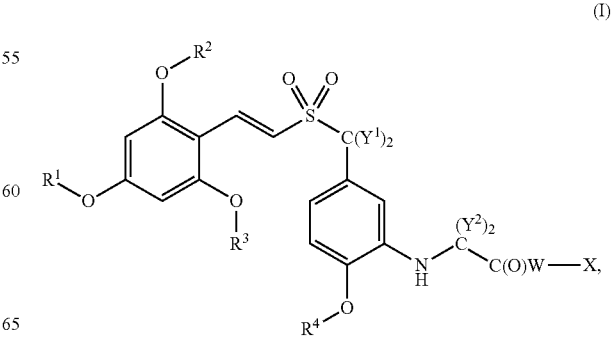

or a pharmaceutically acceptable salt thereof wherein
$R^1$ is $CD_3$ or $CH_3$;
$R^2$ is $CD_3$ or $CH_3$;
$R^3$ is $CD_3$, $CH_3$ or $R^2$;
$R^4$ is $CD_3$ or $CH_3$;
each $Y^1$ is independently hydrogen or deuterium;
each $Y^2$ is independently hydrogen or deuterium;
W is O or NH;
X is hydrogen, $C_1$-$C_7$ alkyl, $C_2$-$C_7$ alkenyl, $C_2$-$C_7$ alkadienyl, $C_6$-$C_{10}$ aryl, 5- to 10-membered heteroaryl,

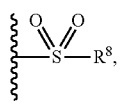

—$CH_2$—$C(O)OR^{12}$ or —$CH(R^{11})$—$C(O)OR^{12}$;
wherein if X is other than —$CH_2$—$C(O)OR^{12}$ or —$CH(R^{11})$—$C(O)OR^{12}$, X is optionally substituted with one or more substituents independently selected from halogen, a —$OC_1$-$C_6$ alkyl group, a 5- to 10-membered heteroaryl group and a 3- to 10-membered heterocycloalkyl wherein the heterocycloalkyl group is optionally substituted with one or more $C_1$-$C_2$ alkyl groups, and wherein if X is $C_1$-$C_7$ alkyl, one or two carbons of the $C_1$-$C_7$ alkyl are optionally replaced with —$NR^5$, and one carbon of the $C_1$-$C_7$ alkyl other than the carbon bonded to the —C(O)O— group of formula I is optionally replaced with oxygen;
each $R^5$ is hydrogen or $C_1$-$C_4$ alkyl optionally substituted with $R^6$; and
each $R^6$ is ($C_1$-$C_4$ alkyl)NH; ($C_1$-$C_4$ alkyl)$_2$N, wherein the ($C_1$-$C_4$) alkyl groups in the ($C_1$-$C_4$ alkyl)$_2$N are the same or different; 3- to 10-membered heterocycloalkyl optionally substituted with $C_1$-$C_2$ alkyl; or $OC_1$-$C_4$ alkyl;
$R^8$ is $C_1$-$C_7$ alkyl, $C_2$-$C_7$ alkenyl, $C_2$-$C_7$ alkadienyl, $C_6$-$C_{10}$ aryl, or 5- to 10-membered heteroaryl; $R^{11}$ is $C_{1-6}$ alkyl, $C_{2-10}$alkoxyalkyl, phenyl, —($C_{1-3}$ alkyl)-($C_{3-6}$ cycloalkyl), or $C_{3-6}$ cycloalkyl, wherein $R^{11}$ is optionally substituted with $C_{1-3}$ alkyl, $C_{1-3}$ alkoxy, phenyl, or —O—(CH$_2$CH$_2$O)$_n$—CH$_3$, wherein n is 1, 2, or 3;
$R^{12}$ is hydrogen; —$C_{1-4}$ alkyl optionally substituted with phenyl; —($C_{3-6}$ cycloalkyl) optionally substituted with phenyl or methyl; —$CH_2$—($C_{3-6}$ cycloalkyl) wherein the $C_{3-6}$ cycloalkyl is optionally substituted with phenyl; phenyl; or biphenyl;
provided that if X is not

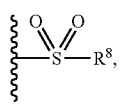

and if each $R^1$, $R^2$, $R^3$, and $R^4$ are each $CH_3$ and each $Y^1$ is hydrogen, then at least one $Y^2$ is deuterium.
In one embodiment of the compound of Formula I, $R^3$ has the value $R^2$ (i.e., $R^2$ and $R^3$ are the same) and the compound of Formula I is a compound of Formula Ia:

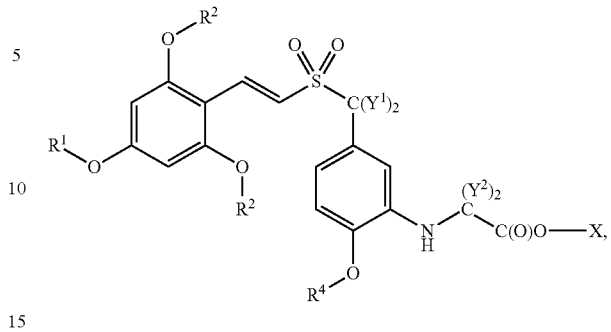

or a pharmaceutically acceptable salt thereof,
wherein each of $R^1$, $R^2$, $R^4$, $Y^1$, $Y^2$, $R^{11}$ and $R^{12}$ is as defined above for a compound of Formula I, and
X is hydrogen, $C_1$-$C_7$ alkyl, $C_2$-$C_7$ alkenyl, $C_2$-$C_7$ alkadienyl, $C_6$-$C_{10}$ aryl, 5- to 10-membered heteroaryl, —$CH_2$—$C(O)OR^{12}$ or —$CH(R^{11})$—$C(O)OR^{12}$.
In one aspect of this embodiment, X is hydrogen, $C_1$-$C_7$ alkyl, $C_2$-$C_7$ alkenyl, $C_2$-$C_7$ alkadienyl, $C_6$-$C_{10}$ aryl, or 5- to 10-membered heteroaryl. In another aspect, X is —$CH_2$—$C(O)OR^{12}$ or —$CH(R^{11})$—$C(O)OR^{12}$.
In one embodiment of the compound of Formula I, $R^3$ has the value $R^2$ (i.e., $R^2$ and $R^3$ are the same) and the compound of Formula I is a compound of Formula Ib:

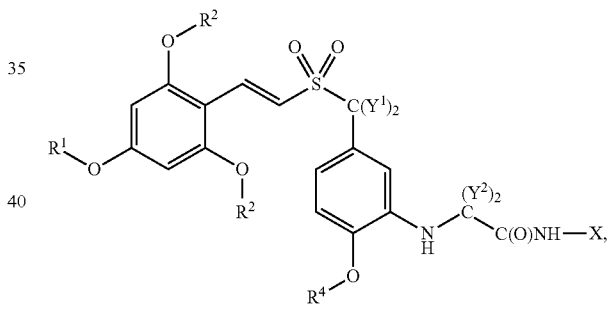

or a pharmaceutically acceptable salt thereof
wherein each variable is as defined above for a compound of Formula I.
In one embodiment of the compound of Formula Ia, $R^2$ is $CD_3$. In one aspect of this embodiment, $R^1$ is $CD_3$. In another aspect of this embodiment, $R^1$ is $CH_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of Formula Ia is a carboxylic acid. In another aspect, the compound of Formula Ia is a pharmaceutically acceptable salt of the carboxylic acid, such as the sodium salt.
In another embodiment of the compound of Formula Ia, $R^2$ is $CH_3$. In one aspect of this embodiment, $R^1$ is $CD_3$. In another aspect of this embodiment, $R^1$ is $CH_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of Formula Ia is a carboxylic acid. In another aspect, the compound of Formula Ia is a pharmaceutically acceptable salt of the carboxylic acid, such as the sodium salt.

In one embodiment of the compound of Formula Ia, $R^1$ is $CD_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of Formula Ia is a carboxylic acid. In another aspect, the compound of Formula Ia is a pharmaceutically acceptable salt of the carboxylic acid, such as the sodium salt.

In another embodiment of the compound of formula Ia, $R^1$ is $CH_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of formula Ia is a carboxylic acid. In another aspect, the compound of formula Ia is a pharmaceutically acceptable salt of the carboxylic acid, such as the sodium salt.

In one embodiment of the compound of formula Ia, $R^4$ is $CD_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of formula Ia is a carboxylic acid. In another aspect, the compound of formula Ia is a pharmaceutically acceptable salt of the carboxylic acid, such as the sodium salt.

In another embodiment of the compound of formula Ia, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of formula Ia is a carboxylic acid. In another aspect, the compound of formula Ia is a pharmaceutically acceptable salt of the carboxylic acid, such as the sodium salt.

In one embodiment of the compound of formula Ia, $R^2$ and $R^1$ are the same. In one aspect of this embodiment, $R^2$ and $R^1$ are $CD_3$. In another aspect of this embodiment, $R^2$ and $R^1$ are $CH_3$.

In one embodiment of formula I, formula Ia or formula Ib, X is $C_1$-$C_7$ alkyl optionally substituted with one or more substituents independently selected from halogen, an —$OC_1$-$C_6$ alkyl group, a 5- to 10-membered heteroaryl group and a 3- to 10-membered heterocycloalkyl wherein the heterocycloalkyl group is optionally substituted with one or more $C_1$-$C_2$ alkyl groups. In one aspect of this embodiment, X is methyl, ethyl, N-morpholinoethyl, $N^1$—($N^4$-methylpiperidinyl)ethyl, pyridylmethyl,

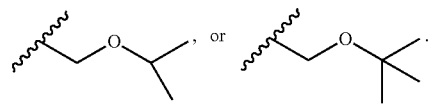

In one embodiment of formula I, formula Ia or formula Ib, X is —$CH_2$—C(O)$OR^{12}$ or —CH($R^{11}$)—C(O)$OR^{12}$. In one aspect of the embodiment wherein X is CH($R^{11}$)—C(O)$OR^{12}$, the compound has the (S) configuration at the carbon bearing $R^{11}$. In certain examples of this embodiment, $R^{11}$ is methyl, ethyl, isopropyl or n-butyl. In certain examples of this embodiment, $R^{12}$ is hydrogen, methyl, ethyl, isopropyl or n-butyl. In certain examples of this embodiment, X is $CH_2CO_2H$; $CH_2CO_2$-methyl; (S)—CH($CO_2H$)-methyl; (S)—CH($CO_2$-methyl)-methyl.

In one embodiment of the compound of Formula Ib, $R^2$ is $CD_3$. In one aspect of this embodiment, $R^1$ is $CD_3$. In another aspect of this embodiment, $R^1$ is $CH_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of Formula Ib is an amide. In another aspect, X is

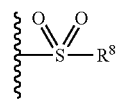

and the compound of Formula Ib is a sulfonamide. In one example of the aspect where X is

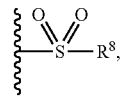

$R^8$ is $C_1$-$C_7$ alkyl, such as methyl or ethyl.

In another embodiment of the compound of Formula Ib, $R^2$ is $CH_3$. In one aspect of this embodiment, $R^1$ is $CD_3$. In another aspect of this embodiment, $R^1$ is $CH_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of Formula Ib is an amide. In another aspect, X is

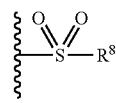

and the compound of Formula Ib is a sulfonamide. In one example of the aspect where X is

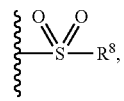

$R^8$ is $C_1$-$C_7$ alkyl, such as methyl or ethyl.

In one embodiment of the compound of Formula Ib, $R^1$ is $CD_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of Formula Ib is an amide. In another aspect, X is

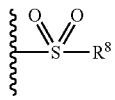

and the compound of Formula Ib is a sulfonamide. In one example of the aspect where X is

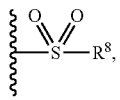

$R^8$ is $C_1$-$C_7$ alkyl, such as methyl or ethyl.

In another embodiment of the compound of Formula Ib, $R^1$ is $CH_3$. In one aspect of this embodiment, $R^4$ is $CD_3$. In another aspect of this embodiment, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of Formula Ib is an amide. In another aspect, X is

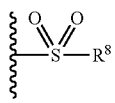

and the compound of Formula Ib is a sulfonamide. In one example of the aspect where X is

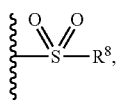

$R^8$ is $C_1$-$C_7$ alkyl, such as methyl or ethyl.

In one embodiment of the compound of Formula Ib, $R^4$ is $CD_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of Formula Ib is an amide. In another aspect, X is

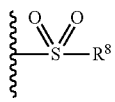

and the compound of Formula Ib is a sulfonamide. In one example of the aspect where X is

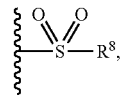

$R^8$ is $C_1$-$C_7$ alkyl, such as methyl or ethyl.

In another embodiment of the compound of Formula Ib, $R^4$ is $CH_3$. In one aspect of this embodiment, each $Y^1$ is deuterium. In another aspect of this embodiment, each $Y^1$ is hydrogen. In one aspect of this embodiment, each $Y^2$ is deuterium. In another aspect of this embodiment, each $Y^2$ is hydrogen. In one aspect of this embodiment, X is hydrogen and the compound of Formula Ib is an amide. In another aspect, X is

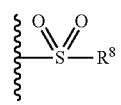

and the compound of Formula Ib is a sulfonamide. In one example of the aspect where X is

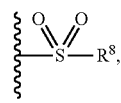

$R^8$ is $C_1$-$C_7$ alkyl, such as methyl or ethyl.

In one embodiment of the compound of Formula Ib, $R^2$ and $R^1$ are the same. In one aspect of this embodiment, $R^2$ and $R^1$ are $CD_3$. In another aspect of this embodiment, $R^2$ and $R^1$ are $CH_3$.

In one embodiment of the compound of formula Ib, X is

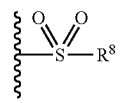

and $R^8$ is $C_1$-$C_7$ alkyl optionally substituted with one or more substituents independently selected from halogen, an —$OC_1$-$C_6$ alkyl group, a 5- to 10-membered heteroaryl group and a 3- to 10-membered heterocycloalkyl wherein the heterocycloalkyl group is optionally substituted with one or more $C_1$-$C_2$ alkyl groups.

In another set of embodiments, any atom not designated as deuterium in any of the embodiments or aspects set forth above is present at its natural isotopic abundance.

In another embodiment, the compound is a compound of formula Ia or Formula IIa wherein X is hydrogen, and wherein the compound is selected from any one of the compounds set forth in Table 1 below:

TABLE 1

| Compound | $R^1$ | $R^2$ | $R^4$ | Each $Y^1$ | Each $Y^2$ |
|---|---|---|---|---|---|
| 100 | $CH_3$ | $CH_3$ | $CH_3$ | H | D |
| 101 | $CH_3$ | $CH_3$ | $CH_3$ | D | H |

TABLE 1-continued

| Compound | R¹ | R² | R⁴ | Each Y¹ | Each Y² |
|---|---|---|---|---|---|
| 102 | CH₃ | CH₃ | CH₃ | D | D |
| 103 | CH₃ | CH₃ | CD₃ | H | H |
| 104 | CH₃ | CH₃ | CD₃ | H | D |
| 105 | CH₃ | CH₃ | CD₃ | D | H |
| 106 | CH₃ | CH₃ | CD₃ | D | D |
| 107 | CH₃ | CD₃ | CH₃ | H | H |
| 108 | CH₃ | CD₃ | CH₃ | H | D |
| 109 | CH₃ | CD₃ | CH₃ | D | H |
| 110 | CH₃ | CD₃ | CH₃ | D | D |
| 111 | CH₃ | CD₃ | CD₃ | H | H |
| 112 | CH₃ | CD₃ | CD₃ | H | D |
| 113 | CH₃ | CD₃ | CD₃ | D | H |
| 114 | CH₃ | CD₃ | CD₃ | D | D |
| 115 | CD₃ | CH₃ | CH₃ | H | H |
| 116 | CD₃ | CH₃ | CH₃ | H | D |
| 117 | CD₃ | CH₃ | CH₃ | D | H |
| 118 | CD₃ | CH₃ | CH₃ | D | D |
| 119 | CD₃ | CH₃ | CD₃ | H | H |
| 120 | CD₃ | CH₃ | CD₃ | H | D |
| 121 | CD₃ | CH₃ | CD₃ | D | H |
| 122 | CD₃ | CH₃ | CD₃ | D | D |
| 123 | CD₃ | CD₃ | CH₃ | H | H |
| 124 | CD₃ | CD₃ | CH₃ | H | D |
| 125 | CD₃ | CD₃ | CH₃ | D | H |
| 126 | CD₃ | CD₃ | CH₃ | D | D |
| 127 | CD₃ | CD₃ | CD₃ | H | H |
| 128 | CD₃ | CD₃ | CD₃ | H | D |
| 129 | CD₃ | CD₃ | CD₃ | D | H |
| 130 | CD₃ | CD₃ | CD₃ | D | D | or a pharmaceutically acceptable salt thereof, such as the sodium salt, wherein any atom not designated as deuterium is present at its natural isotopic abundance.

In another embodiment, the compound is a compound of formula Ib wherein X is

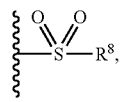

R⁸ is CH₃, and wherein the compound is selected from any one of the compounds set forth in Table 2 below:

TABLE 2

| Compound | R¹ | R² | R⁴ | Each Y¹ | Each Y² |
|---|---|---|---|---|---|
| 200 | CH₃ | CH₃ | CH₃ | H | D |
| 201 | CH₃ | CH₃ | CH₃ | D | H |
| 202 | CH₃ | CH₃ | CH₃ | D | D |
| 203 | CH₃ | CH₃ | CD₃ | H | H |
| 204 | CH₃ | CH₃ | CD₃ | H | D |
| 205 | CH₃ | CH₃ | CD₃ | D | H |
| 206 | CH₃ | CH₃ | CD₃ | D | D |
| 207 | CH₃ | CD₃ | CH₃ | H | H |
| 208 | CH₃ | CD₃ | CH₃ | H | D |
| 209 | CH₃ | CD₃ | CH₃ | D | H |
| 210 | CH₃ | CD₃ | CH₃ | D | D |
| 211 | CH₃ | CD₃ | CD₃ | H | H |
| 212 | CH₃ | CD₃ | CD₃ | H | D |
| 213 | CH₃ | CD₃ | CD₃ | D | H |
| 214 | CH₃ | CD₃ | CD₃ | D | D |
| 215 | CD₃ | CH₃ | CH₃ | H | H |
| 216 | CD₃ | CH₃ | CH₃ | H | D |
| 217 | CD₃ | CH₃ | CH₃ | D | H |
| 218 | CD₃ | CH₃ | CH₃ | D | D |
| 219 | CD₃ | CH₃ | CD₃ | H | H |
| 220 | CD₃ | CH₃ | CD₃ | H | D |
| 221 | CD₃ | CH₃ | CD₃ | D | H |
| 222 | CD₃ | CH₃ | CD₃ | D | D |
| 223 | CD₃ | CD₃ | CH₃ | H | H |
| 224 | CD₃ | CD₃ | CH₃ | H | D |
| 225 | CD₃ | CD₃ | CH₃ | D | H |
| 226 | CD₃ | CD₃ | CH₃ | D | D |
| 227 | CD₃ | CD₃ | CD₃ | H | H |
| 228 | CD₃ | CD₃ | CD₃ | H | D |
| 229 | CD₃ | CD₃ | CD₃ | D | H |
| 230 | CD₃ | CD₃ | CD₃ | D | D | or a pharmaceutically acceptable salt thereof, such as the sodium salt, wherein any atom not designated as deuterium is present at its natural isotopic abundance.

In one embodiment of any of the compounds of table 1 or pharmaceutically acceptable salts thereof wherein R¹ is CD₃, the isotopic enrichment factor for the deuterium atoms of the R¹ CD₃ group is at least 5500 (82.5% deuterium incorporation), at least 6000 (90% deuterium incorporation), or at least 6333.3 (95% deuterium incorporation); wherein any atom not designated as deuterium is present at its natural isotopic abundance.

In one embodiment of any of the compounds of table 1 or pharmaceutically acceptable salts thereof wherein R² is CD₃, the isotopic enrichment factor for the deuterium atoms of the R² CD₃ group is at least 5500 (82.5% deuterium incorporation), at least 6000 (90% deuterium incorporation), or at least 6333.3 (95% deuterium incorporation); wherein any atom not designated as deuterium is present at its natural isotopic abundance.

In one embodiment of any of the compounds of table 1 or pharmaceutically acceptable salts thereof wherein R⁴ is CD₃, the isotopic enrichment factor for the deuterium atoms of the R⁴ CD₃ group is at least 5500 (82.5% deuterium incorporation), at least 6000 (90% deuterium incorporation), or at least 6333.3 (95% deuterium incorporation); wherein any atom not designated as deuterium is present at its natural isotopic abundance.

In one embodiment of any of the compounds of table 1 or pharmaceutically acceptable salts thereof wherein each Y¹ is deuterium, the isotopic enrichment factor for the deuterium atoms of the resulting CD₂ group is at least 5500 (82.5% deuterium incorporation), at least 6000 (90% deuterium incorporation), or at least 6333.3 (95% deuterium incorporation); wherein any atom not designated as deuterium is present at its natural isotopic abundance.

In one embodiment of any of the compounds of table 1 or pharmaceutically acceptable salts thereof wherein each Y² is deuterium, the isotopic enrichment factor for the deuterium atoms of the resulting CD₂ group is at least 5500 (82.5% deuterium incorporation), at least 6000 (90% deuterium incorporation), or at least 6333.3 (95% deuterium incorporation); wherein any atom not designated as deuterium is present at its natural isotopic abundance.

In one embodiment of any of the compounds of table 2 or pharmaceutically acceptable salts thereof wherein R¹ is CD₃, the isotopic enrichment factor for the deuterium atoms of the R¹ CD₃ group is at least 5500 (82.5% deuterium incorporation), at least 6000 (90% deuterium incorporation), or at least 6333.3 (95% deuterium incorporation); wherein any atom not designated as deuterium is present at its natural isotopic abundance.

In one embodiment of any of the compounds of table 2 or pharmaceutically acceptable salts thereof wherein $R^2$ is $CD_3$, the isotopic enrichment factor for the deuterium atoms of the $R^2$ $CD_3$ group is at least 5500 (82.5% deuterium incorporation), at least 6000 (90% deuterium incorporation), or at least 6333.3 (95% deuterium incorporation); wherein any atom not designated as deuterium is present at its natural isotopic abundance.

In one embodiment of any of the compounds of table 2 or pharmaceutically acceptable salts thereof wherein $R^4$ is $CD_3$, the isotopic enrichment factor for the deuterium atoms of the $R^4$ $CD_3$ group is at least 5500 (82.5% deuterium incorporation), at least 6000 (90% deuterium incorporation), or at least 6333.3 (95% deuterium incorporation); wherein any atom not designated as deuterium is present at its natural isotopic abundance.

In one embodiment of any of the compounds of table 2 or pharmaceutically acceptable salts thereof wherein each $Y^1$ is deuterium, the isotopic enrichment factor for the deuterium atoms of the resulting $CD_2$ group is at least 5500 (82.5% deuterium incorporation), at least 6000 (90% deuterium incorporation), or at least 6333.3 (95% deuterium incorporation); wherein any atom not designated as deuterium is present at its natural isotopic abundance.

In one embodiment of any of the compounds of table 2 or pharmaceutically acceptable salts thereof wherein each $Y^2$ is deuterium, the isotopic enrichment factor for the deuterium atoms of the resulting $CD_2$ group is at least 5500 (82.5% deuterium incorporation), at least 6000 (90% deuterium incorporation), or at least 6333.3 (95% deuterium incorporation); wherein any atom not designated as deuterium is present at its natural isotopic abundance.

The invention in one embodiment is also directed to intermediates having the following structures:

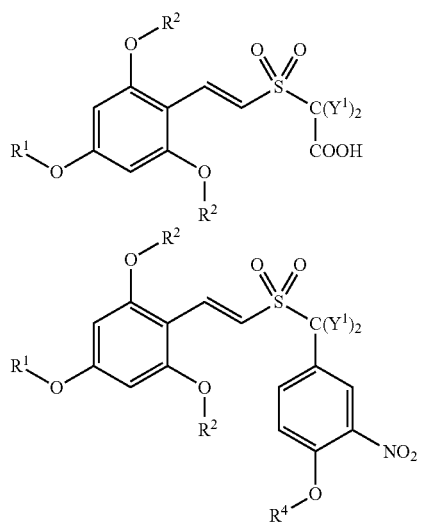

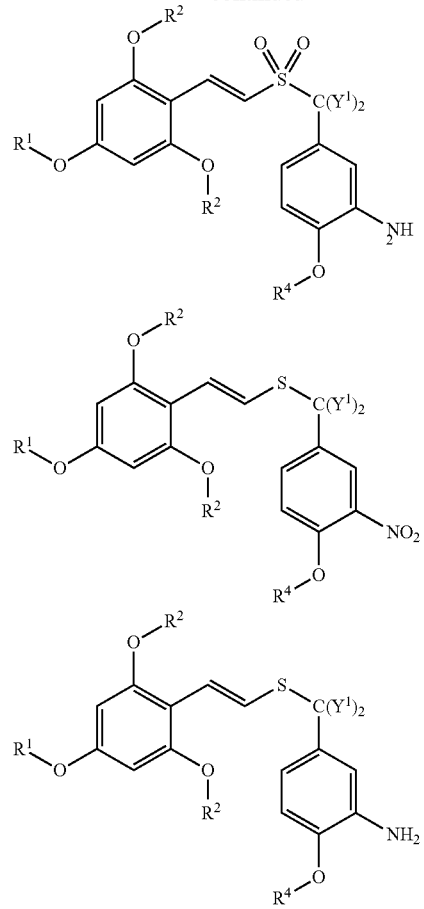

or salts thereof, wherein $R^1$, $R^2$, $R^4$ and $Y^1$ are defined as in formula I or Ia.

In another set of embodiments, any atom not designated as deuterium in any of the foregoing embodiments or aspects or examples is present at its natural isotopic abundance.

The synthesis of compounds disclosed herein can be readily achieved by synthetic chemists of ordinary skill by reference to the Exemplary Synthesis and Examples disclosed herein.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

Compounds disclosed herein, such as compounds of formula Ia, may be readily prepared in a manner analogous to those described in U.S. Pat. No. 7,598,232, such as in Schemes 1-10 of the '232 patent, and references cited therein, or in a manner analogous to the one described in Reddy et al., J. Med. Chem., 2011, 54, 6254-6276, in each case using suitable deuterated reagents depending on the desired deuteration pattern.

Compounds of formula Ia may be prepared from other compounds of formula Ia in accordance with Scheme 1, shown below:

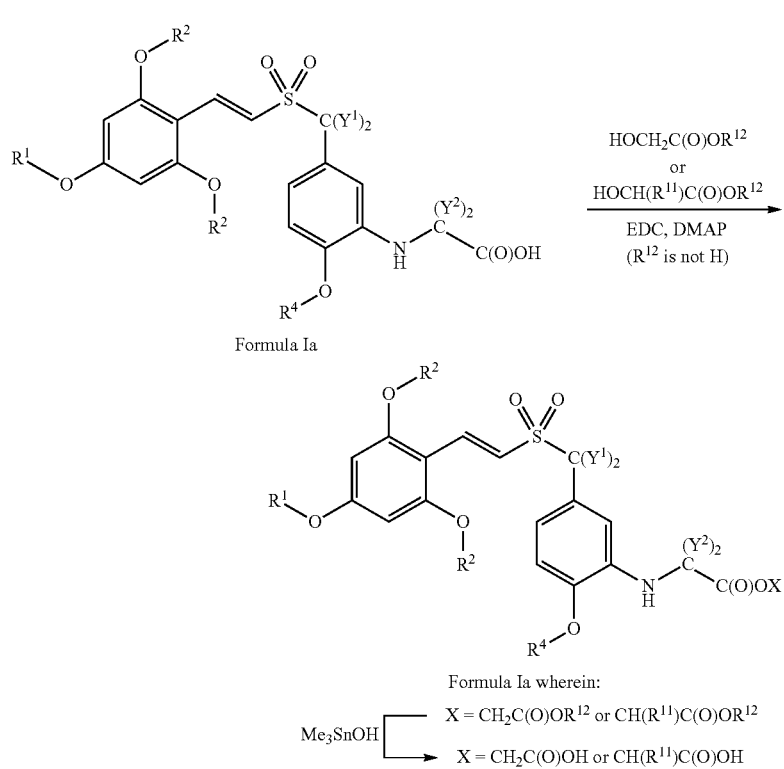

Formula Ia

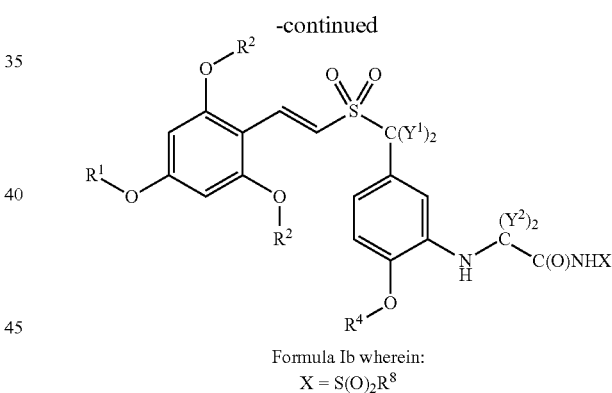

Formula Ia wherein:
X = CH$_2$C(O)OR$^{12}$ or CH(R$^{11}$)C(O)OR$^{12}$

Me$_3$SnOH → X = CH$_2$C(O)OH or CH(R$^{11}$)C(O)OH

As shown in Scheme 1, a compound of formula Ia wherein X is CH$_2$C(O)OR$^{12}$ or CH(R$^{11}$)C(O)OR$^{12}$ or CH$_2$C(O)OH or CH(R$^{11}$)C(O)OH may be prepared by treating a compound of formula Ia wherein X is hydrogen with either of the hydroxyesters shown in Scheme 1. The resulting phenylamino ester of formula Ia may be converted to the corresponding acid if desired.

Compounds of formula Ib may be prepared from compounds of formula Ia in accordance with Scheme 2, shown below:

Scheme 2: preparation of compounds of formula Ib wherein X is

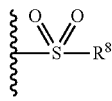

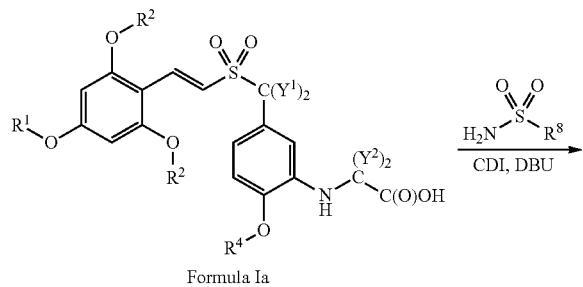

Formula Ia

-continued

[structure]

Formula Ib wherein:
X = S(O)$_2$R$^8$

As shown in Scheme 2, a compound of formula Ib wherein X is

[structure]

may be prepared starting with a compound of formula Ia wherein X is hydrogen by treating it with sulfonamide R$^8$S(O)$_2$NH$_2$.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of the formulae herein and their synthetic precursors, including those within routes not explicitly shown in Schemes herein, are within the means of chemists of ordinary skill in the art. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pharmaceutical compositions comprising an effective amount of a compound of Formula I (e.g., including any of the formulae herein such as Formula Ia and Ib or Formula II and IIa), or a pharmaceutically acceptable salt thereof; and an acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterallyacceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Such administration is known to be effective with erectile dysfunction drugs: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of the present invention further comprises a second therapeutic agent. The second therapeutic agent includes any compound or therapeutic agent known to have or that demonstrates advantageous properties when administered with an anti-angiogenic or an anti-neoplastic agent. Such agents are described in detail in U.S. Pat. No. 5,635,517, as well as in PCT patent publications WO2005097125, WO2005055929, WO2004041190, WO2006060507, WO2006058008, WO2006053160, WO2005044178, WO2004100953, WO2006089150, WO2006036892, WO2006018182, WO2005082415, WO2005048942, WO2005042558, WO2005035714 and WO2005027842; and in United States Patent publications US2005100529, US2006030594, US2005143344 and US2006079461, each of the foregoing of which describes second therapeutic agents that may be combined with rigosertib. In one embodiment, the second therapeutic agent is an agent that is useful for the treatment of myelodysplastic syndrome (MDS) or for delaying transition of myelodysplastic syndrome (MDS) to acute myeloid leukemia (AML).

In one embodiment, the second therapeutic agent is an agent that is useful for the treatment of solid tumors, ovarian cancer, pancreatic cancer, hepatoma, ovarian cancer, breast cancer, colon cancer, renal cancer, AML, or lymphocytic leukemia.

In one embodiment, the second therapeutic agent is an agent that is useful a) in the treatment of one or more of the following diseases or conditions: primary or metastatic tumor or neoplastic cells in cancers of at least the following histologic subtypes: sarcoma (cancers of the connective and other tissue of mesodermal origin); melanoma (cancers deriving from pigmented melanocytes); carcinoma (cancers of epithelial origin); adenocarcinoma (cancers of glandular epithelial origin); cancers of neural origin (glioma/glioblastoma and astrocytoma); and hematological neoplasias, such as leukemias and lymphomas (e.g., acute lymphoblastic leukemia, chronic lymphocytic leukemia, acute lymphocytic leukemia, acute myeloid leukemia, and chronic myeloid leukemia); b) to kill primary or metastatic tumor or neoplastic cells in cancers having their origin in at least the following organs or tissues, regardless of histologic subtype: breast; tissues of the male and female urogenital system (e.g. ureter, bladder, prostate, testis, ovary, cervix, uterus, vagina); lung; tissues of the gastrointestinal system (e.g., stomach, large and small intestine, colon, rectum); exocrine glands such as the pancreas and adrenals; tissues of the mouth and esophagus; brain and spinal cord; kidney (renal); pancreas; hepatobiliary system (e.g., liver, gall bladder); lymphatic system; smooth and striated muscle; bone and bone marrow; skin; and tissues of the eye; c) in the treatment of cancers or tumors in any prognostic stage of development, as measured, for example, by the "Overall Stage Groupings" (also called "Roman Numeral") or the Tumor, Nodes, and Metastases (TNM) staging systems. Appropriate prognostic staging systems and stage descriptions for a given cancer are known in the art, for example as described in http://cancer-net.nci.nih.gov/pdq/pdq_treatment.shtml and/or d) in the treatment of non-cancer proliferative disorders. Non-cancer proliferative disorders are characterized by the uncontrolled growth of cells with a benign phenotype, meaning that the cells evade only the normal controls on growth, but cannot metastasize. Non-cancer proliferative disorders which may be treated with the present compounds include, but are not limited to, the following: hemangiomatosis in newborn; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Dupuytren's fibrosis, cirrhosis, atherosclerosis and vascular restenosis.

In another preferred embodiment, the second therapeutic agent is selected from gemcitabine, oxaliplatin, irinotecan, and combinations thereof.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., 1966, Cancer Chemother Rep, 50: 219. Body surface area may be approximately determined from height and weight of the patient. See, e.g., Scientific Tables, Geigy Pharmaceuticals, Ardsley, N.Y., 1970, 537. An effective amount of a compound of this invention can range from about 0.005 mg/kg to about 200 mg/kg, such as from about 0.05 mg/kg to about 100 mg/kg, more preferably 0.1 mg/kg to about 75 mg/kg, more preferably 0.5 mg/kg to about 60 mg/kg.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al, eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting phosphatidylinositol 3-kinase (PI3-K) and polo-like kinase 1 (PLK-1) in a cell, comprising contacting a cell with a compound of Formula I (e.g., including any of the formulae herein such as Formula Ia and Ib or Formula II and IIa) herein.

According to another embodiment, the invention provides a method of treating a disease or condition that may be treated by rigosertib, comprising the step of administering to a subject an effective amount of a compound or a composition of this invention.

In one embodiment, the disease is myelodysplastic syndrome (MDS), solid tumors, ovarian cancer, pancreatic cancer, hepatoma, ovarian cancer, breast cancer, colon cancer, renal cancer, AML, or lymphocytic leukemia. In one embodiment, the disease is myelodysplastic syndrome (MDS). In one embodiment, the invention provides a method of delaying transition of myelodysplastic syndrome (MDS) to acute myelogenous leukemia (AML), comprising the step of administering to the patient an effective amount of a compound or a composition of this invention.

Identifying a patient in need of such treatment can be in the judgment of a patient or a health care professional and can be subjective (e.g. opinion) or objective (e.g. measurable by a test or diagnostic method).

In another embodiment, the above method of treatment comprises the further step of co-administering to the patient one or more second therapeutic agents. The choice of second therapeutic agent may be made from any second therapeutic agent known to be useful for co-administration with rigosertib. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a patient does not preclude the separate administration of that same therapeutic agent, any other second therapeutic agent or any compound of this invention to the patient at another time during a course of treatment.

Effective amounts of these second therapeutic agents are well known to those skilled in the art and guidance for dosing may be found in patents and published patent applications referenced herein, as well as in Wells et al, eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a patient, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above.

Another aspect of the invention is a compound of Formula I for use in the treatment or prevention in a patient of a disease, disorder or symptom thereof delineated herein.

EXAMPLE 1. EVALUATION OF METABOLIC STABILITY

Microsomal Assay:
Human liver microsomes (20 mg/mL) are obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) are purchased from Sigma-Aldrich.

Determination of Metabolic Stability:
7.5 mM stock solutions of test compounds are prepared in DMSO. The 7.5 mM stock solutions are diluted to 12.5-50 μM in acetonitrile (ACN). The 20 mg/mL human liver microsomes are diluted to 0.625 mg/mL in 0.1 M potassium phosphate buffer, pH 7.4, containing 3 mM MgCl$_2$. The diluted microsomes are added to wells of a 96-well deep-well polypropylene plate in triplicate. A 10 μL aliquot of the 12.5-50 μM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 μM test compound, and 2 mM NADPH in 0.1 M potassium phosphate buffer, pH 7.4, and 3 mM MgCl$_2$. The reaction mixtures are incubated at 37° C., and 50 μL aliquots are removed at 0, 5, 10, 20, and 30 minutes and added to shallow-well 96-well plates which contain 50 μL of ice-cold ACN with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compound of Formula I and the positive control, 7-ethoxycoumarin (1 μM). Testing is done in triplicate.

Data Analysis:
The in vitro $t_{1/2}$s for test compounds are calculated from the slopes of the linear regression of % parent remaining (ln) vs incubation time relationship.

in vitro $t_{1/2}$=0.693/$k$ $k$=−[slope of linear regression of % parent remaining (ln) vs incubation time]

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:
1. A compound of Formula II:

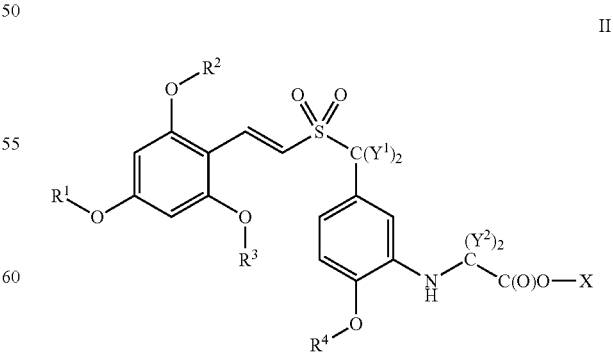

or a pharmaceutically acceptable salt thereof wherein
R$^1$ is CD$_3$ or CH$_3$;
R$^2$ is CD$_3$ or CH$_3$;

R³ is CD₃, CH₃ or R²;
R⁴ is CD₃ or CH₃;
each Y¹ is independently hydrogen or deuterium;
each Y² is independently hydrogen or deuterium;
X is hydrogen, $C_1$-$C_7$ alkyl, $C_2$-$C_7$ alkenyl, $C_2$-$C_7$ alkadienyl, $C_6$-$C_{10}$ aryl or 5- to 10-membered heteroaryl, wherein X is optionally substituted with one or more substituents independently selected from halogen, a —$OC_1$-$C_6$ alkyl group, a 5- to 10-membered heteroaryl group and a 3- to 10-membered heterocycloalkyl wherein the heterocycloalkyl group is optionally substituted with one or more $C_1$-$C_2$ alkyl groups, and wherein if X is $C_1$-$C_7$ alkyl, one or two carbons of the $C_1$-$C_7$ alkyl are optionally replaced with —NR⁵, and one carbon of the $C_1$-$C_7$ alkyl other than the carbon bonded to the —C(O)O— group of formula II is optionally replaced with oxygen;
each R⁵ is hydrogen or $C_1$-$C_4$ alkyl optionally substituted with R⁶; and
each R⁶ is ($C_1$-$C_4$ alkyl)NH; ($C_1$-$C_4$ alkyl)₂N, wherein the ($C_1$-$C_4$) alkyl groups in the ($C_1$-$C_4$ alkyl)₂N are the same or different; 3- to 10-membered heterocycloalkyl optionally substituted with $C_1$-$C_2$ alkyl; or $OC_1$-$C_4$ alkyl;
provided that if each R', R², R³, and R⁴ are each CH₃ and each Y¹ is hydrogen, then at least one Y² is deuterium;
wherein
any atom not designated as deuterium is present at its natural isotopic abundance, and wherein the deuterium incorporation at each atom designated as deuterium is at least 90%.

2. The compound of claim 1, represented by structural Formula IIa:

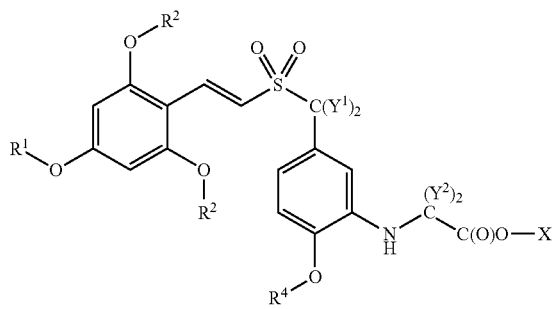

IIa or a pharmaceutically acceptable salt thereof.

3. The compound of claim 1, wherein R² is CD₃.
4. The compound of claim 1, wherein R² is CH₃.
5. The compound of claim 1, wherein R¹ is CD₃.
6. The compound of claim 1, wherein R¹ is CH₃.
7. The compound of claim 1, wherein R⁴ is CD₃.
8. The compound of claim 1, wherein R⁴ is CH₃.
9. The compound of claim 1, wherein each Y¹ is deuterium.
10. The compound of claim 1, wherein each Y¹ is hydrogen.
11. The compound of claim 1, wherein each Y² is deuterium.
12. The compound of claim 1, wherein each Y² is hydrogen.
13. The compound of claim 1, wherein X is hydrogen and the compound is a carboxylic acid, or a pharmaceutically acceptable salt thereof.

14. The compound of claim 2 wherein X is hydrogen, wherein the compound is selected from any one of the compounds set forth in Table 1 below:

| R¹ | R² | R⁴ | Each Y¹ | Each Y² |
|---|---|---|---|---|
| CH₃ | CH₃ | CH₃ | H | D |
| CH₃ | CH₃ | CH₃ | D | H |
| CH₃ | CH₃ | CH₃ | D | D |
| CH₃ | CH₃ | CD₃ | H | H |
| CH₃ | CH₃ | CD₃ | H | D |
| CH₃ | CH₃ | CD₃ | D | H |
| CH₃ | CH₃ | CD₃ | D | D |
| CH₃ | CD₃ | CH₃ | H | H |
| CH₃ | CD₃ | CH₃ | H | D |
| CH₃ | CD₃ | CH₃ | D | H |
| CH₃ | CD₃ | CH₃ | D | D |
| CH₃ | CD₃ | CD₃ | H | H |
| CH₃ | CD₃ | CD₃ | H | D |
| CH₃ | CD₃ | CD₃ | D | H |
| CH₃ | CD₃ | CD₃ | D | D |
| CD₃ | CH₃ | CH₃ | H | D |
| CD₃ | CH₃ | CH₃ | D | H |
| CD₃ | CH₃ | CH₃ | D | D |
| CD₃ | CH₃ | CD₃ | H | H |
| CD₃ | CH₃ | CD₃ | H | D |
| CD₃ | CH₃ | CD₃ | D | H |
| CD₃ | CH₃ | CD₃ | D | D |
| CD₃ | CD₃ | CH₃ | H | H |
| CD₃ | CD₃ | CH₃ | H | D |
| CD₃ | CD₃ | CH₃ | D | H |
| CD₃ | CD₃ | CH₃ | D | D |
| CD₃ | CD₃ | CD₃ | H | H |
| CD₃ | CD₃ | CD₃ | H | D |
| CD₃ | CD₃ | CD₃ | D | H |
| CD₃ | CD₃ | CD₃ | D | D | or a pharmaceutically acceptable salt thereof.

15. A pharmaceutical composition comprising a compound of claim 1, and a pharmaceutically acceptable carrier.

16. The composition of claim 15, additionally comprising a second therapeutic agent selected from gemcitabine, oxaliplatin, and irinotecan, or combinations thereof.

17. A method of treating a disease or condition selected from myelodysplastic syndrome (MDS), solid tumors, ovarian cancer, pancreatic cancer, hepatoma, breast cancer, colon cancer, renal cancer, AML, or lymphocytic leukemia, in a subject, the method comprising the step of administering to the subject the compound of claim 1.

18. The method of claim 17, wherein the disease is myelodysplastic syndrome.

19. A compound of Formula I:

(I)

or a pharmaceutically acceptable salt thereof wherein
R¹ is CD₃ or CH₃;
R² is CD₃ or CH₃;

$R^3$ is $CD_3$, $CH_3$ or $R^2$;
$R^4$ is $CD_3$ or $CH_3$;
each $Y^1$ is independently hydrogen or deuterium;
each $Y^2$ is independently hydrogen or deuterium;
W is O or NH;
X is hydrogen, $C_1$-$C_7$ alkyl, $C_2$-$C_7$ alkenyl, $C_2$-$C_7$ alkadienyl, $C_6$-$C_{10}$ aryl, 5- to 10-membered heteroaryl,

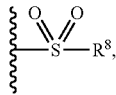

—$CH_2$—$C(O)OR^{12}$ or —$CH(R^{11})$—$C(O)OR^{12}$;
wherein if X is other than —$CH_2$—$C(O)OR^{12}$ or —$CH(R^{11})$—$C(O)OR^{12}$, X is optionally substituted with one or more substituents independently selected from halogen, a —$OC_1$-$C_6$ alkyl group, a 5- to 10-membered heteroaryl group and a 3- to 10-membered heterocycloalkyl wherein the heterocycloalkyl group is optionally substituted with one or more $C_1$-$C_2$ alkyl groups, and wherein if X is $C_1$-$C_7$ alkyl, one or two carbons of the $C_1$-$C_7$ alkyl are optionally replaced with —$NR^5$, and one carbon of the $C_1$-$C_7$ alkyl other than the carbon bonded to the —C(O)O— group of formula I is optionally replaced with oxygen;
each $R^5$ is hydrogen or $C_1$-$C_4$ alkyl optionally substituted with $R^6$; and
each $R^6$ is ($C_1$-$C_4$ alkyl)NH; ($C_1$-$C_4$ alkyl)$_2$N, wherein the ($C_1$-$C_4$) alkyl groups in the ($C_1$-$C_4$ alkyl)$_2$N are the same or different; 3- to 10-membered heterocycloalkyl optionally substituted with $C_1$-$C_2$ alkyl; or $OC_1$-$C_4$ alkyl;
$R^8$ is $C_1$-$C_7$ alkyl, $C_2$-$C_7$ alkenyl, $C_2$-$C_7$ alkadienyl, $C_6$-$C_{10}$ aryl, or 5- to 10-membered heteroaryl; $R^{11}$ is $C_{1-6}$ alkyl, $C_{2-10}$ alkoxyalkyl, phenyl, —($C_{1-3}$ alkyl)-($C_{3-6}$ cycloalkyl),
or $C_{3-6}$ cycloalkyl, wherein $R^{11}$ is optionally substituted with $C_{1-3}$ alkyl, $C_{1-3}$ alkoxy, phenyl, or —O—($CH_2CH_2O$)$_n$—$CH_3$, wherein n is 1, 2, or 3;
$R^{1-2}$ is hydrogen; —$C_{1-4}$ alkyl optionally substituted with phenyl; —($C_{3-6}$ cycloalkyl) optionally substituted with phenyl or methyl; —$CH_2$—($C_{3-6}$ cycloalkyl) wherein the $C_{3-6}$ cycloalkyl is optionally substituted with phenyl; phenyl; or biphenyl;
provided that if X is not

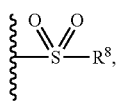

and if each $R^1$, $R^2$, $R^3$, and $R^4$ are each $CH_3$ and each $Y^1$ is hydrogen, then at least one $Y^2$ is deuterium; wherein any atom not designated as deuterium is present at its natural isotopic abundance, and wherein the deuterium incorporation at each atom designated as deuterium is at least 90%.

20. A compound of claim 19, wherein $R^2$ and $R^3$ are the same and the compound of Formula I is a compound of Formula Ia:

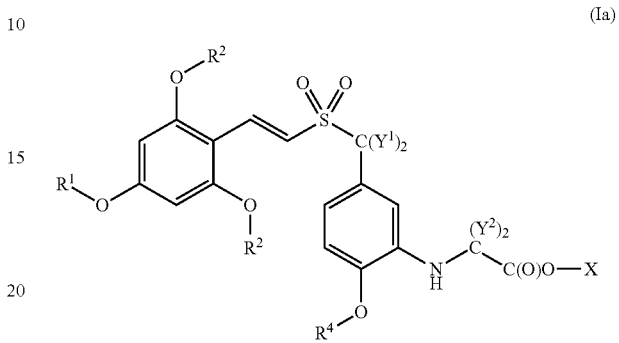

or a pharmaceutically acceptable salt thereof,
wherein
X is hydrogen, $C_1$-$C_7$ alkyl, $C_2$-$C_7$ alkenyl, $C_2$-$C_7$ alkadienyl, $C_6$-$C_{10}$ aryl, 5- to 10-membered heteroaryl, —$CH_2$—$C(O)OR^{12}$ or —$CH(R^{11})$—$C(O)OR^{12}$; and
each of $R^1$, $R^2$, $R^4$, $Y^1$, $Y^2$, $R^{11}$ and $R^{12}$ is as defined above for a compound of Formula I in claim 19.

21. A compound of claim 19, wherein $R^2$ and $R^3$ are the same and the compound of Formula I is a compound of Formula Ib:

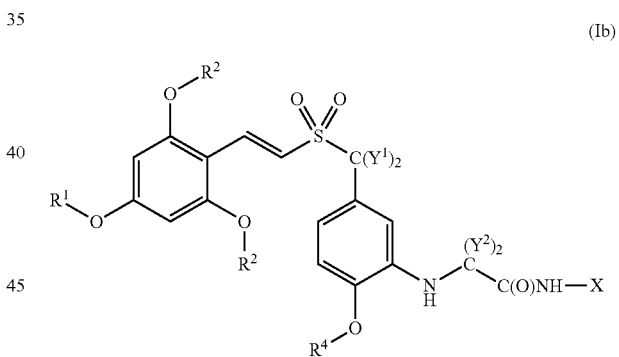

or a pharmaceutically acceptable salt thereof.

22. A compound of claim 1, wherein the deuterium incorporation at each atom designated as deuterium is at least 95%.

23. A compound of claim 19, wherein the deuterium incorporation at each atom designated as deuterium is at least 95%.

* * * * *

UNITED STATES PATENT AND TRADEMARK OFFICE
CERTIFICATE OF CORRECTION

PATENT NO. : 9,840,463 B2  
APPLICATION NO. : 15/010961  
DATED : December 12, 2017  
INVENTOR(S) : Tung Page 1 of 1

It is certified that error appears in the above-identified patent and that said Letters Patent is hereby corrected as shown below:

In the Claims

In Column 29, Claim 1, Line 25, delete "R'" and insert --$R^1$--.

In Column 29, Claim 2, Line 33, delete "Ha:" and insert --IIa:--.

In Column 31, Claim 19, Line 43, delete "$R^{1-2}$", and insert --$R^{12}$--.

Signed and Sealed this  
Seventh Day of August, 2018

Andrei Iancu  
*Director of the United States Patent and Trademark Office*